US005697361A

United States Patent [19]

Smith

[11] Patent Number: 5,697,361

[45] Date of Patent: Dec. 16, 1997

[54] INDUCTION PUMP METHOD FOR INCREASED BREATHABLE AIR FLOW OF COOLED AND REDUCED HUMIDITY AIR

[76] Inventor: William C. Smith, 7701 Whiterim Ter., Potomac, Md. 20854

[21] Appl. No.: 563,409

[22] Filed: Nov. 28, 1995

Related U.S. Application Data

[60] Continuation of Ser. No. 188,750, Jan. 31, 1994, abandoned, which is a division of Ser. No. 952,041, Sep. 28, 1992, abandoned.

[51] Int. Cl.[6] .......... A61M 16/00; A62B 7/00; A62B 9/00; F24F 5/00

[52] U.S. Cl. .......... 128/204.25; 128/204.18; 128/205.29; 128/204.15

[58] Field of Search .......... 128/200.24, 202.13, 128/204.15, 204.24, 204.29, 205.11, 204.25, 204.18, 205.29

[56] References Cited

U.S. PATENT DOCUMENTS

| | | | |
|---|---|---|---|
| 1,922,920 | 1/1933 | Aherne | 210/40 |
| 1,952,281 | 3/1934 | Ranque | 62/170 |
| 3,319,627 | 5/1967 | Windsor | 128/204.25 |
| 3,717,147 | 2/1973 | Flynn | 128/204.25 |
| 3,875,745 | 4/1975 | Franklin | 60/319 |
| 3,906,996 | 9/1975 | DePass et al. | 137/604 |
| 4,237,877 | 12/1980 | Boehler | 128/204.15 |
| 4,300,496 | 11/1981 | Price | 128/202.13 |
| 4,448,111 | 5/1984 | Doherty | 98/38 E |
| 4,501,270 | 2/1985 | Ulinskas | 128/202.13 |
| 4,552,140 | 11/1985 | Cowley et al. | 128/201.25 |
| 4,649,912 | 3/1987 | Collins | 128/202.13 |
| 4,850,809 | 7/1989 | Smith | 417/76 |
| 4,883,051 | 11/1989 | Westenskow | 128/204.21 |
| 5,237,987 | 8/1993 | Anderson | 128/204.18 |

FOREIGN PATENT DOCUMENTS

| | | | |
|---|---|---|---|
| 132021 | 6/1992 | Germany | 128/204.25 |
| 13662 | 6/1914 | United Kingdom | 128/204.25 |
| 17972 | 7/1914 | United Kingdom | 128/204.25 |
| 173310 | 12/1921 | United Kingdom | 128/204.15 |
| 718080 | 11/1954 | United Kingdom | 128/204.25 |

OTHER PUBLICATIONS

Free Air Pumps, E.D. Bullard Company brouchure, 1990.

Gast Multi-Venturi Vacuum Generators, Gast Manufacturing Corp. brouchure, 1990.

Bullard Free-Air Instruction Manuel, pp. 1,6,7. E.D. Bullard Co. Rt. 7, Box 596, Cynthiana KY 41031 1991.

Airverter Family, brochure, Smith-Eastern Corp, Beltsville, MD 1 page.

30 C.F.R. part 11, subpart J, 11. 122(b).

*Primary Examiner*—Kimberly L. Asher

*Attorney, Agent, or Firm*—Tom Hamill, Jr.

[57] ABSTRACT

This invention increases the flow of breathable air from an air pump to an enclosure such as a hood or enclosed structure without requiring an increase in the air pump output. The invention involves interposing an jet venturi induction pump in the conduit between the air pump and the enclosure. Breathable filtered, muffled, and metered ambient air is induced into the jet venturi induction pump, thereby increasing the flow of breathable air into the enclosure without an increase in the air pump output. In addition, the jet venturi induction pump cools and reduces the humidity of the air emitted from the air pump.

1 Claim, 5 Drawing Sheets

INDUCTION PUMP METHOD FOR INCREASED BREATHABLE AIR FLOW OF COOLED AND REDUCED HUMIDITY AIR

This application is a continuation of application Ser. No. 08/188,750, filed Jan. 31, 1994, now abandoned, which was a division of application Ser. No. 07/952,041, filed Sep. 28, 1992, now abandoned.

BACKGROUND OF THE INVENTION

This invention relates to apparatus for providing breathable air to enclosures such as respiratory devices, face masks, hoods, and structures or work areas.

Breathable air must be supplied to persons doing underwater diving as well as welding, sandblasting, spraying chemicals or paint, or working in contained or enclosed areas such as manholes and underground conduits, or during maintenance to furnaces, boilers or drying kilns.

The term "breathable air" as used in this disclosure is air containing at least 19.5 percent oxygen. It is referred to as Grade D air in 30 C.F.R. part 11, Subpart J, 11,122 (b). Breathable air supplied to enclosures must be free of toxic contaminants such as carbon monoxide, oil vapors, and oil mist.

Breathable air must be supplied to an "enclosure", used in this disclosure to indicate any enclosed device, structure, or area which must be provided with breathable air. Examples include supplied air hoods, full- and half- mask respirators, and structures such as equipment lockers, manholes, conduits, structures housing machinery and electrical equipment, engines of any type, furnaces, and boilers.

Increasingly stringent working environmental air quality standards as administered by OSHA have created a growing demand for breathable air supplies in the workplace. There is a need for the inexpensive supply of large amounts of breathable air.

Air pumps are used to supply breathable air for enclosures because an air pump is capable of supplying air free of toxic contaminants. Air pumps provide a relatively high volume of air (10 cfm) at a relatively low pressure (5 psig). The construction of an air pump typically involves rotary vanes and seals manufactured of carbon which require close tolerances and are relatively expensive to manufacture.

Air pumps are to be distinguished from air compressors, which deliver a relatively low volume of air (4 cfm) at a relatively high pressure (80 to 100 psig). The construction of air compressors involves pistons and cylinders. Such compressors are relatively inexpensive to manufacture but operate at relatively high temperatures, develop oil mists, and create problems with the generation of toxic contaminants.

The process of compressing air inevitably involves increase in the temperature and humidity of the air. It is desirable to lower the temperature and humidity of the air before use in order to reduce fatigue and increase the endurance of the user. Air provided by an air pump is commonly cooled by coiling some 50 feet of air hose in a 55 gallon drum which is then filled with crushed ice and water. The air passes through the coiled cooled tube before reaching the user. This process requires a supply of ice and water and imposes frictional loss in air pressure in the air provided to the user.

This invention increases the supply of breathable air delivered to an enclosure by an air pump without a concomitant increase in the output of the air pump. In addition, the temperature and humidity of the air is reduced.

U.S. Pat. No. 4,850,809 by William C. Smith discloses an apparatus for converting high pressure, low volume air to low pressure, high volume air for use in atomizing fluids such as paint. This apparatus includes a jet venturi induction pump which uses a venturi jet to create a low pressure field and induce ambient air into the air stream. This apparatus includes means for metering the air flow volume into an atomizing process and for mixing gasses provided to the atomizer.

U.S. Pat. No. 3,906,996 discloses a regulator having variable side wall openings which control the dilution of oxygen passing from a source of oxygen to a face mask. The oxygen is diluted by entraining ambient air.

U.S. Pat. No. 1,922,920 discloses an adjustable diffuser and injector in which sterilizing gas or liquid is drawn into a converging stream of liquid under pressure.

U.S. Pat. No. 1,952,281 discloses a vortex tube apparatus which provides cooled gas. In a vortex tube, compressed gas enters a tangentially drilled tube and is forced to spin down the tube toward a hot air control valve. Hot gas emerges from one end of the tube and cold gas from the other. A vortex tube does not involve a venturi jet.

Multi-venturi vacuum generators use the venturi principle to create a vacuum and are operated by compressed air. Such vacuum generators are not used to supply breathable air. Gast Multi-Venturi Vacuum Generators, Gast Manufacturing Corp., Benton Harbor, Mich., 1990.

The present invention interposes a jet venturi induction pump into the conduit between an air pump and an enclosure. The jet venturi induction pump induces ambient breathable air into the air stream. This additional air approximately doubles the flow of air to the enclosures, without significantly reducing the air pressure. The use of a jet venturi induction pump also cools the air which had been significantly heated by the air pump. Additionally, a substantial reduction in humidity is noted in the air supplied by this invention. The reduction in heat and humidity reduces the discomfort of the user of the breathable air.

None of the prior art inventions achieves the objectives of this invention, that of increasing the output of an air pump and reducing the heat and humidity of the supplied air. This invention reduces the cost of providing breathable air and also improves the comfort of the user. The portability of this invention is of significant value to the user. Additionally, it meters the induced air to accomodate the application.

SUMMARY OF THE INVENTION

This invention is a low cost means to allow an approximate doubling of the capacity of an air pump to supply breathable air to an enclosure of any type. It consists of an air pump connected by a conduit to an enclosure and a jet venturi induction pump located in the conduit. The jet venturi induction pump is without working parts and requires virtually no maintenance. The jet venturi induction pump induces breathable air into the conduit and also cools and partially dehumidifies the breathable air provided by the air pump. The invention includes embodiments of the jet venturi induction pump which muffle the sound of the jet venturi induction pump, filters the air induced into the jet venturi induction pump, and which meters the amount of air induced into the jet venturi induction pump.

An objective of the invention is to enhance the provision of breathable air supplied to an enclosure by an air pump without increasing the output of the air pump.

Another objective is to enhance the provision of breathable air supplied to an enclosure by an air pump without increasing the energy consumed by the air pump.

Another objective is to supply breathable air at reduced pressure to enclosures.

Another objective is to increase the number of enclosures which may be supplied with breathable air from a single air pump.

Another objective is to provide enhanced amounts of filtered breathable air to an enclosure.

Another objective is to provide means for metering breathable air supplied to an enclosure.

A final objective is to provide breathable air meeting OSHA and NIOSH standards to an enclosure at approximately half the cost of conventional means and with minimal environmental impact.

DESCRIPTION OF THE PREFERRED EMBODIMENTS

Figure 1:
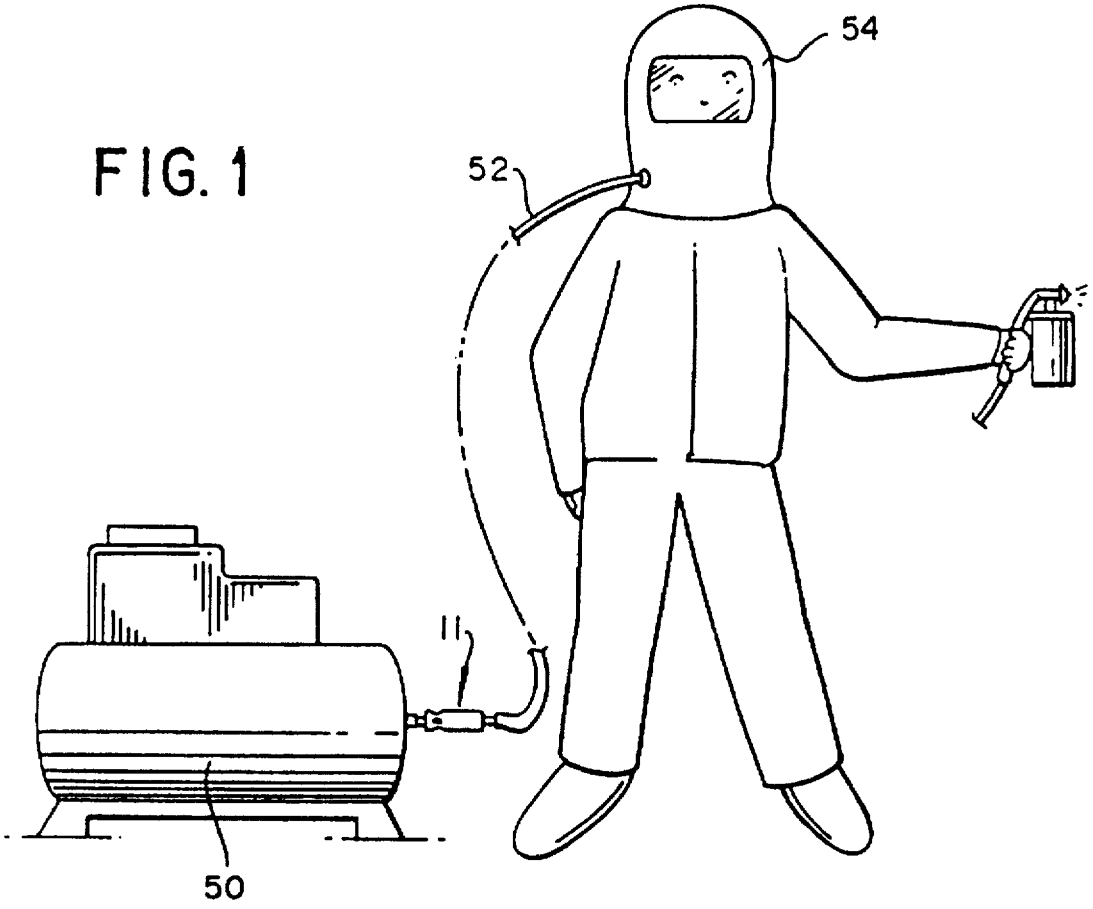
FIG. 1 is a schematic diagram showing the invention providing breathable air to a hood or respiratory device.

FIG. 1 is a schematic view of the invention used to supply breathable air to a person wearing a respiratory device such as a hood 54. An air pump 50 provides breathable air to a jet venturi induction pump 11. A conduit or hose 52 connects the jet venturi induction pump to the hood.

Figure 2:
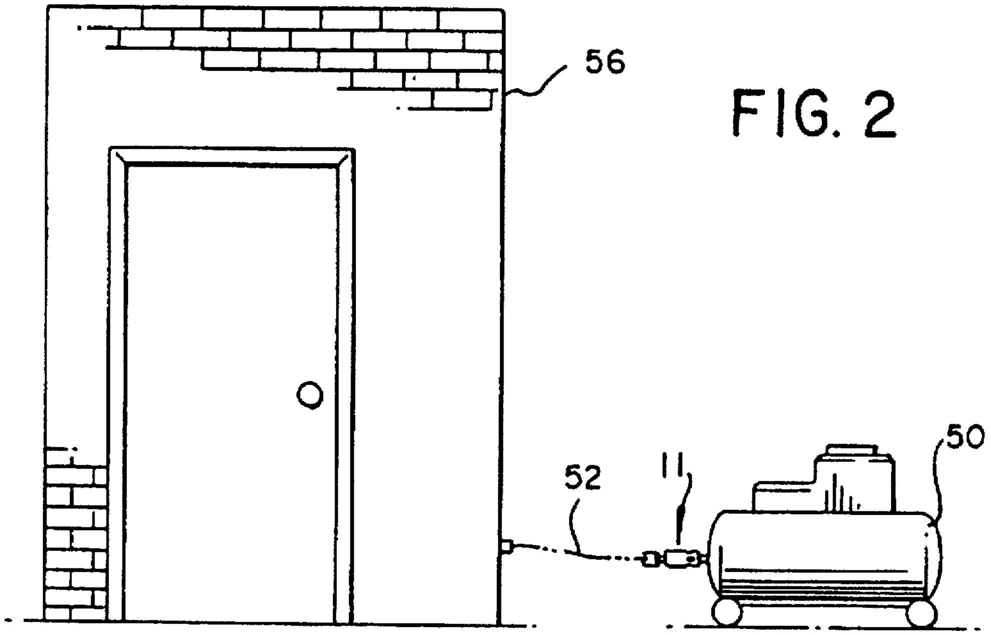
FIG. 2 is a schematic diagram showing the invention providing breathable air to a structure.

FIG. 2 is a schematic view of the invention used to supply breathable air to a structure or enclosure 56. An air pump 50 provides breathable air to an jet venturi induction pump 11. A hose 52 connects the jet venturi induction pump to the structure or enclosure.

Figure 9:
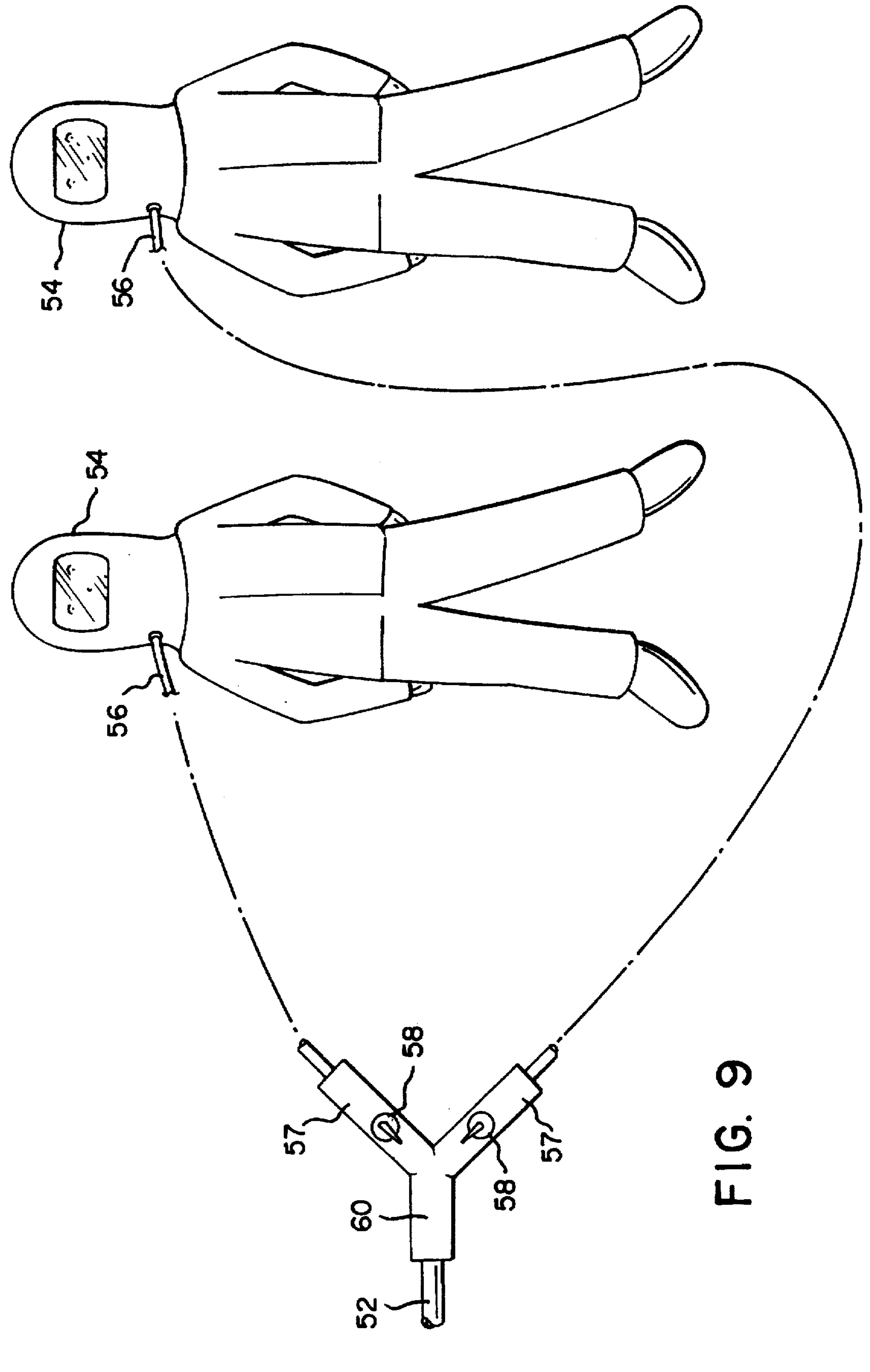
FIG. 9 is a schematic diagram showing the invention providing breathable air to two hoods.

FIG. 9 shows an arrangement whereby a single air pump with a jet venturi induction pump may be used to provide breathable air to more than one enclosure. An air pump and jet venturi induction pump are used to provide breathable air to hose 52 as shown in FIGS. 1 and 2. Hose 52 is connected to a Y-connector 60 with arms 57. Each arm of the Y-connector has a ball-valve 58 which controls passage of breathable air through the arm. Hoses 56 convey breathable air to the hoods 54.

This invention may be used to supply breathable air to a wide array of enclosures. This includes user wearable enclosures such as a hood, divers helmet, a full facepiece respirator, a half mask respirator, or any type of respiratory device. In addition, this invention may be used to supply breathable air to relatively small structural enclosures, such as an electrical equipment locker, large conduit, mine, tunnel, furnace, kiln, boiler, welding booth, sandblasting booth, or other enclosure. Since this invention provides large amounts of breathable air, a single air pump may be used in this invention to supply breathable air to several enclosures. Factors which determine the number of enclosures served include the capacity of the air pump, design of the jet venturi induction pump, distance of the users from the air pump, and the requirements of the users.

It is essential that breathable air, i.e. air containing at least 19.5% oxygen, be available at the air intake of the air pump and at the induction ducts or intakes of the jet venturi induction pump.

Any air pump which provides breathable air at a maximum outlet air pressure of about 15 psig may be used. Such air pumps do not produce carbon monoxide, oil vapor, oil mist or moisture. They generally are equipped with inlet and outlet filters which minimize the particles in the breathable air.

The conduit connecting the jet venturi induction pump and the enclosure preferable is a hose or pipe but may be any other suitable sort of permissible conduit such as defined in Title 30 C.F.R. Part II "Permissability of Respiratory Protection Devices." The only additional requirement is that the conduit be of sufficient internal diameter to accommodate the volume of breathable air emerging from the jet venturi induction pump outlet.

Any induction pump or device which allows the induction into an airstream of a large volume of breathable air without substantially reducing the pressure of the airstream may be used in this invention. A preferred induction pump is described as a jet venturi jet venturi induction pump, 11 in FIGS. 3 and 4 in U.S. Pat. No. 4,850,809, incorporated herein by reference.

Figure 3:
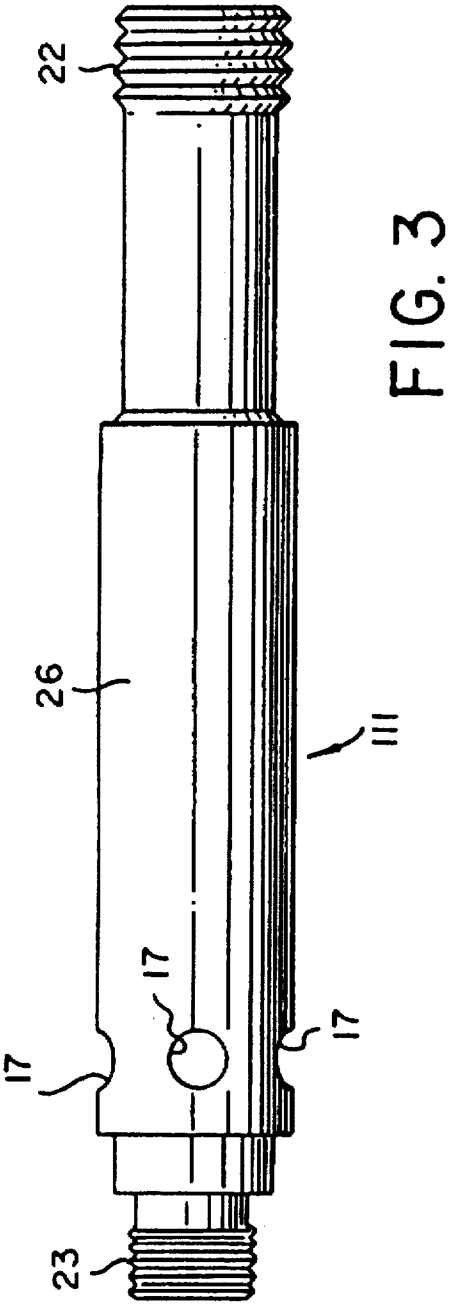
FIG. 3 is a side elevation view of the first embodiment of the jet venturi induction pump.

FIG. 3 is a side elevation Of the first embodiment jet venturi induction pump 11. The pump has an elongated cylindrical body 26 with an inlet coupling 23 which is connected to output of the air pump and an outlet coupling 22 which is attached to the conduit leading to the enclosure. In this preferred embodiment, four induction duct ports 17 are arrayed about or along the circumference of the jet venturi induction pump at the end nearest the inlet coupling. The number of induction duct ports may range from one to a multiplicity.

Figure 6:
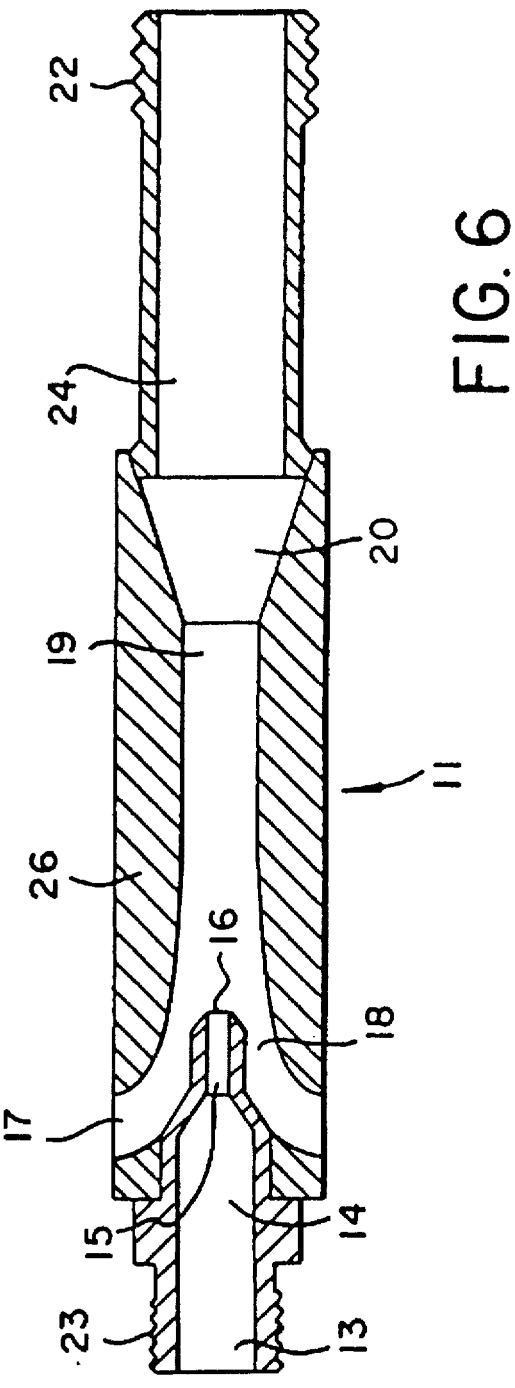
FIG. 6 is a longitudinal cross sectional view of the jet venturi induction pump of FIG. 3.

FIG. 6 is a central longitudinal cross sectional view of the first embodiment jet venturi induction pump 11. The jet venturi induction pump is connected with the outlet of the air pump via inlet coupling 23. Breathable air from the air pump enters the jet venturi induction pump through the nozzle entrance area 13. At region 14 the breathable air from the air pump converges at the throat of the venturi nozzle 15, wherein the air pump air velocity is maximized, thereby reducing pressure, temperature, and humidity. The high velocity causes below ambient pressure air to exit at 16, which is called the free jet area. The region 16 may also be described as a low pressure field. At this point, external breathable ambient air received at one atmosphere pressure flows to the low pressure field region 16 through the induction duct ports 17. The ambient air mixes with the low pressure air duct air in the upstream section of the inductor at 18 and flows toward the area 19 called the pressure recovery section where finalizing of the breathable air occurs at the divergent section of the venturi 20. The breathable air exits the jet venturi induction pump at the outlet area 24. The jet venturi induction pump is connected to the conduit by the outlet connector 22.

It is important to the proper operation of the jet venturi induction pump that the diameter of the nozzle entrance area 13 be approximately equal to the diameter of the pressure recovery section 19. The approximate equality of the diameters of the nozzle entrance area and the pressure recovery section is important to all jet venturi induction pump embodiments.

It pressure of the breathable air in the pressure recovery section is always less that the pressure in the nozzle entrance area. The ratio of pressures is dependent on the volume of breathable air induced through the induction duct ports. The ratio of pressure nozzle entrance area:pressure recovery section may be as great as 10:1.

Figure 4:
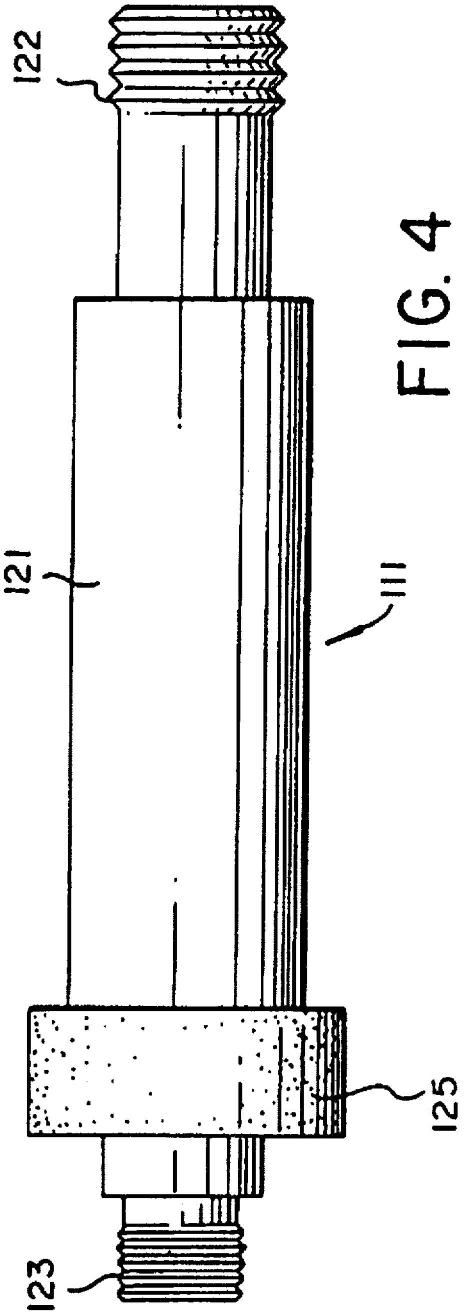
FIG. 4 is a side elevation view of the second embodiment of the jet venturi induction pump.

FIG. 4 is a side elevation of the second embodiment jet venturi induction pump 111. The pump has an elongated cylindrical body 126 with an inlet coupling 123 which is connected to output of the air pump and an outlet coupling 122 which is attached to the conduit leading to the enclosure. A cylindrical sleeve 121 covers a portion of the surface of the jet venturi induction pump. The sleeve may be moved slid or moved longitudinally along the surface of the jet venturi induction pump. The sleeve may be positioned to cover all or part of the induction duct ports. The sleeve controls and meters the amount of breathable air induced by the jet venturi induction pump. In FIG. 4 the jet venturi induction pump is shown with jet venturi induction ports covered. A cylindrical porous filter muffler 125 is connected to the end of the sleeve nearest to the jet venturi induction duct ports and covers the portions of the induction duct ports which are not covered by the sleeve. The muffler both reduces the noise of the jet venturi induction pump and filters the air entering the induction duct ports.

Figure 7:
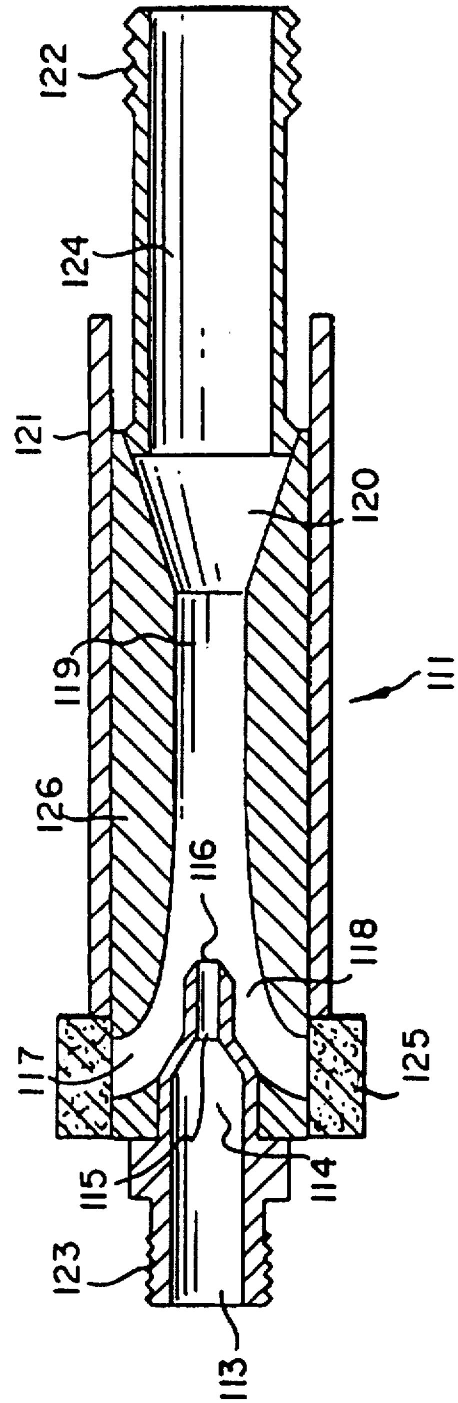
FIG. 7 is a longitudinal cross sectional view of the jet venturi induction pump of FIG. 4.

FIG. 7 is a central longitudinal cross sectional view of the second embodiment jet venturi induction pump 111. The jet venturi induction pump is connected with the outlet of the air pump via inlet coupling 123. Breathable air from the air pump enters the jet venturi induction pump through the nozzle entrance area 113. At region 114 the breathable air from the air pump converges at the throat of the venturi nozzle 115, wherein the air pump air velocity is maximized. The high velocity causes below ambient pressure air to exit at 116 and which is called the free jet area. The region 116 may also be described as a low pressure field. At this point, external breathable ambient air received at one atmosphere pressure flows to the low pressure field region 116 through the induction duct ports 117. A cylindrical sleeve 121 may be used to cover all or a portion of the induction duct ports. In FIG. 7 the sleeve is in a position which leaves the induction duct ports uncovered. A cylindrical porous filter muffler 125 is attached to the cylindrical sleeve and covers the portion of the induction duct ports which are not covered by the sleeve 121.

The ambient air mixes with the low pressure air pump air in the upstream section of the inductor at 118 and flows toward the area 119 called the pressure recovery section where finalizing of the breathable air occurs at the divergent section of the venturi 120. The breathable air exits the jet venturi induction pump at the outlet area 124. The jet venturi induction pump is connected to the conduit by the outlet connector 122.

Figure 5:
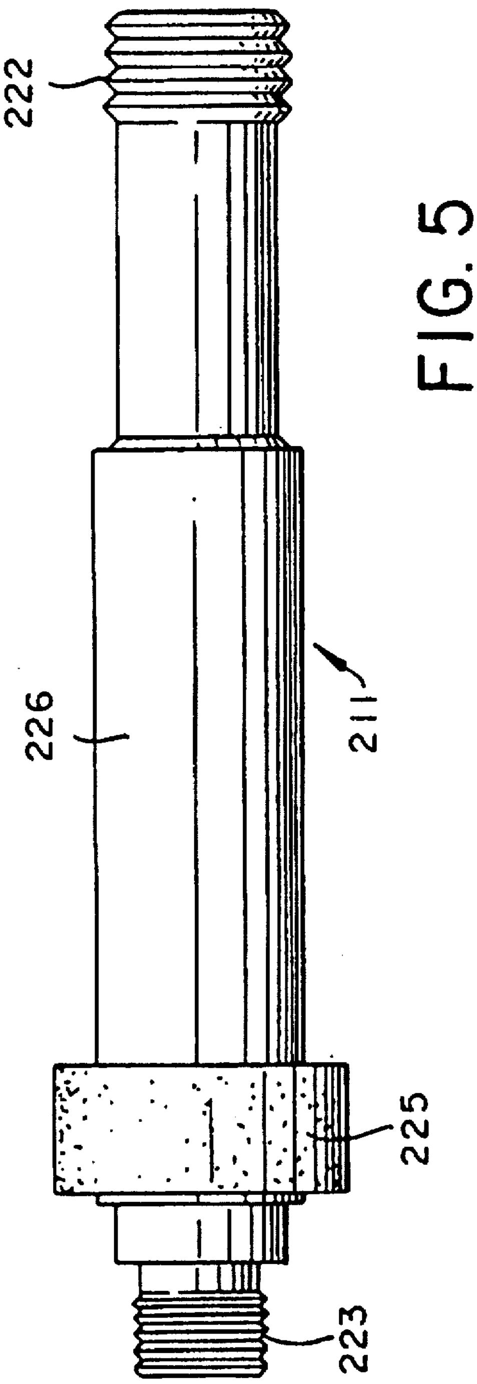
FIG. 5 is a side elevation view of the third embodiment of the jet venturi induction pump.

FIG. 5 is a side elevation of the third embodiment jet venturi induction pump 211. The pump has an elongated cylindrical body 226 with an inlet coupling 223 which is connected to output of the air pump and an outlet coupling 222 which is attached to the conduit leading to the enclosure. A cylindrical porous filter muffler 225 covers the jet venturi induction duct ports. The muffler both reduces the noise of the jet venturi induction pump and filters the air entering the induction duct ports.

Figure 8:
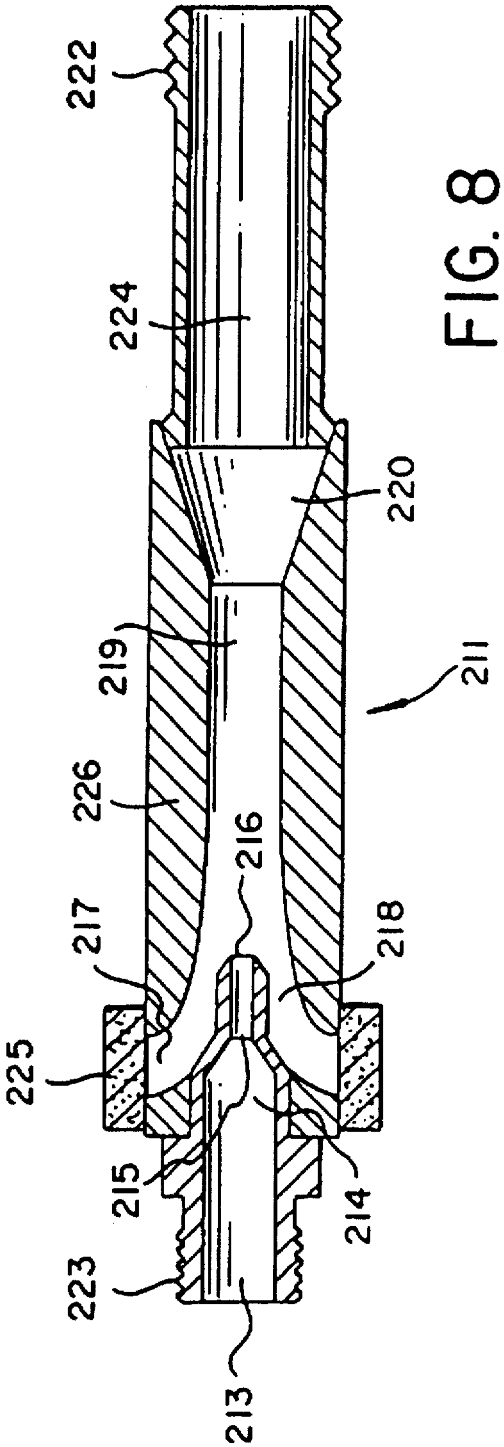
FIG. 8 is a longitudinal cross sectional view of the jet venturi induction pump of FIG. 5.

FIG. 8 is a central longitudinal cross sectional view of the third embodiment jet venturi induction pump 211. The jet venturi induction pump is connected with the outlet of the air pump via inlet coupling 223. Breathable air from the air pump enters the jet venturi induction pump through the nozzle entrance area 213. At region 214 the breathable air from the air pump converges at the throat of the venturi nozzle 215, wherein the air pump air velocity is maximized. The high velocity causes below ambient pressure air to exit at 216 and which is called the free jet area. The region 216 may also be described as a low pressure field. At this point, external breathable ambient air received at one atmosphere pressure flows to the low pressure field region 216 through the induction duct ports 217. The jet venturi induction duct ports are covered by a porous filter muffler material which has the dual function of reducing the sound of the jet venturi induction pump and of filtering the breathable ambient area which enters through the jet venturi induction duct ports. The ambient air mixes with the low pressure air duct air in the upstream section of the inductor at 218 and flows toward the area 219 called the pressure recovery section where finalizing of the breathable air occurs at the divergent section of the venturi 220. The breathable air exits the jet venturi induction pump at the outlet area 224. The jet venturi induction pump is connected to the conduit to the enclosure by the outlet connector 222.

The jet venturi induction pump of embodiments one, two and three and the sleeve of embodiment two may be made of any suitable hard, strong, and resistant material, such as aluminum, steel, brass, or hard plastic. Aluminum is a preferred material. The muffler may be made of any suitable porous filtering material, such as steel or synthetic polymer filter material. A synthetic polymer filter with a 5 micron pore size is preferred.

In operation, the air pump supplies breathable air in the range of 4 to 15 cfm at a pressure of 3 to 15 psig. Breathable ambient air is induced into the airstream with the resulting supply of approximate twice the cfm of breathable air at a lower pressure than that from the air pump. High pressure in the enclosure is undesirable. High pressure creates noise and turbulence within the enclosure. In addition, when many hoods are used, the air stream impinges directly upon the user's forehead, which is unpleasant over an extended period of time and contributes to feelings of annoyance, discomfort, and fatigue. The amount of air induced into the jet venturi induction pump may be controlled using the sleeve in the embodiment two jet venturi induction pump. The external noise of the jet venturi induction pump may be reduced and the number of particles in the induced air may be reduced using the mufflers of embodiment two and three jet venturi induction pumps.

The jet venturi induction pump cools the air in two ways. Compression of air is always associated with heating. The air emitted from an air pump is always significantly heated compared with the ambient air. Passage through the jet venturi jet venturi induction pump, however, involves an increase in speed of air movement and an expansion of the air which is always associated with cooling. In addition, the jet venturi induction pump induces ambient air, which dilutes the air emitted from the air pump, thereby cooling the resulting stream of air.

Air which passes through the jet venturi induction pump has the further benefit of lowered humidity. This probably is a result of the cooling effect of the jet venturi induction pump. The reduced pressure, cooling, and reduction of relative humidity caused by the jet venturi induction pump provides breathable air which minimizes annoyance, discomfort, and fatigue to the user.

EXAMPLE 1

A Bullard EDP10 FREE-AIR pump, produced by E. D. Bullard Company, Cynthiana, Ky., was used to supply filtered breathable air developing 10 cfm at 15 psig. FREE-AIR is a trademark of E. D. Bullard Company for air pumps. An AIRVERTER jet venturi jet venturi induction pump was attached to the air pump outlet. AIRVERTER is a trademark owned by Smith Eastern Corporation, Beltsville, Md., for a low pressure high volume spray system. An embodiment two jet venturi induction pump was used. The output of the jet venturi induction pump was 18 cfm at 6 psig.

EXAMPLE 2

The apparatus of Example 1 was used. The temperature of the ambient air in the room was 80° F. The air pump was operated at 10 psig. After 15 minutes of operation, the temperature of the output of the air pump was 115° F. The temperature of air from the jet venturi induction pump was 85° F. Over a period of three hours operation, the temperature of the output from the jet venturi induction pump was consistently about 25° F. below the temperature of the output from the air pump. Over the same period, the relative humidity of the output air from the jet venturi induction pump was consistently about 45% lower than the relative humidity of the output air from the air pump.

It will be apparent to those skilled in the art that the examples and embodiments described herein are by way of illustration and not of limitation, and that other examples may be utilized without departing from the spirit and scope of the present invention, as set forth in the appended claims.

I claim:

1. A process for reducing the temperature and humidity of breathable air having a temperature and relative humidity above that of ambient air due to compression by an air pump, and supplying such breathable air to a user wearable enclosure comprising the steps of:

a) passing the compressed breathable air at a pressure of between 3–15 psig and a flow rate of 4–15 cfm, through a jet venturi induction pump having induction ports for permitting the entry of non-compressed breathable air, b) inducing non-compressed breathable air at ambient air temperature and ambient humidity into said jet venturi induction pump through said induction ports, c) mixing the compressed breathable air with the non-compressed breathable air in the jet venturi induction pump, and d) conveying the mixed breathable air which has about twice the flow rate and about half the pressure of the compressed breathable air through a conduit from the jet venturi induction pump to said user wearable enclosure, said mixed breathable air having its air temperature reduced by up to 25 degrees Fahrenheit, and its relative humidity reduced by up to 45 percent, as compared to said compressed breathable air, whereby the user is provided with breathable air which has been significantly reduced in temperature and humidity from said compressed breathable air.

* * * * *